(12) United States Patent
Collet et al.

(10) Patent No.: US 12,324,710 B2
(45) Date of Patent: Jun. 10, 2025

(54) METHOD FOR DISASSEMBLING A MARKER ARRAY FROM AN ARRAY FIXATION, AND ARRAY ASSEMBLY FOR PERFORMING SAID METHOD

(71) Applicant: DePuy Ireland Unlimited Company, Ringaskiddy (IE)

(72) Inventors: Hervé Collet, Gieres (FR); Nicolas Demanget, Gieres (FR); Elie Fournier, Sassenage (FR); Alasdair Mercer, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 1145 days.

(21) Appl. No.: 17/074,950

(22) Filed: Oct. 20, 2020

(65) Prior Publication Data

US 2021/0113294 A1 Apr. 22, 2021

(30) Foreign Application Priority Data

Oct. 22, 2019 (EP) .................................... 19204708

(51) Int. Cl.
*A61B 90/00* (2016.01)
*A61B 34/30* (2016.01)
*A61B 34/20* (2016.01)

(52) U.S. Cl.
CPC .............. *A61B 90/39* (2016.02); *A61B 34/30* (2016.02); *A61B 2034/2055* (2016.02); *A61B 2090/3937* (2016.02); *A61B 2090/3983* (2016.02); *A61B 2090/3991* (2016.02); *A61B 2560/0266* (2013.01)

(58) Field of Classification Search
CPC ............ A61B 90/39; A61B 2090/2055; A61B 2090/3937; A61B 2090/3983; A61B 2090/3991; A61B 34/30; A61B 2034/2055; A61B 2560/0266
See application file for complete search history.

(56) References Cited

U.S. PATENT DOCUMENTS

| | | | |
|---|---|---|---|
| 7,840,256 B2 | 11/2010 | Lakin et al. | |
| 2005/0215888 A1 | 9/2005 | Grimm et al. | |
| 2008/0051768 A1 | 2/2008 | Stumpf et al. | |
| 2015/0351863 A1 | 12/2015 | Plassky et al. | |
| 2019/0000372 A1* | 1/2019 | Gullotti | A61B 17/7091 |

FOREIGN PATENT DOCUMENTS

| | | |
|---|---|---|
| EP | 2124797 B1 | 10/2014 |
| EP | 3247305 A1 | 11/2017 |

* cited by examiner

*Primary Examiner* — Chao Sheng
(74) *Attorney, Agent, or Firm* — Condo Roccia Koptiw LLP

(57) ABSTRACT

The disclosure relates to a method for disassembling a marker array (10) comprising at least three optical markers (100) arranged according a determined array geometry configured to be tracked by a localization camera from an array fixation (11) to which the marker array (10) is connected, the method comprising, prior to or during disconnecting the marker array (10) from the array fixation (11), actuating a mechanism configured to selectively modify the array geometry so as to unable tracking of the marker array by the localization camera.

20 Claims, 7 Drawing Sheets

METHOD FOR DISASSEMBLING A MARKER ARRAY FROM AN ARRAY FIXATION, AND ARRAY ASSEMBLY FOR PERFORMING SAID METHOD

CROSS-REFERENCE TO RELATED APPLICATIONS

This application claims priority under 35 U.S.C. § 119 to European Application No. 19204708.2, filed Oct. 22, 2019, which is incorporated herein by reference in its entirety.

FIELD OF THE DISCLOSURE

The present disclosure relates to a method for disassembling a marker array from an array fixation, and an array assembly for performing said method. Such an array assembly is advantageously used in surgical procedures.

BACKGROUND OF THE DISCLOSURE

Some surgical interventions are carried out by a robot configured to treat an anatomical structure of a patient according to a surgical plan. To that end, the robot may carry a surgical tool, such as a saw, a burr, a drill, etc. in order to maintain the tool in a suitable position to achieve the surgical plan. The surgical tool may be held by a surgeon to implement the surgical plan.

Although the patient's anatomical structure may be maintained in a fixed position during the surgical intervention, e.g. by being attached to the operating table, it may slightly move. Besides, the surgeon may also induce small movements of the tool or the robot during the surgical procedure.

In order to compensate for such small relative movements of the tool and the anatomical structure, the robot may be configured to constantly align the tool with the planned treated region. To that end, the position of the tool relative to the patient's anatomical structure may be tracked in real time by a localization system. For example, marker arrays may be rigidly attached by an array fixation to the anatomical structure and to the robot and/or the tool. Each marker array comprises a plurality of optical markers (at least three) that are arranged according to a specific geometry, which is detectable by a camera of the localization system.

Document WO 2018/103945 teaches a robot carrying a surgical saw configured to compensate for small relative movements of the anatomical structure and the saw blade, in order to constantly align the plane of the saw blade with a planned cutting plane.

FIG. 1 illustrates an embodiment of said robot 1 during knee arthroplasty, the saw blade 2 being cutting the tibia. A marker array 11 is rigidly attached to the femur F, a marker array 12 is rigidly attached to the tibia T and a marker array 13 is rigidly attached to the saw 2 or to the robot. Said marker arrays are in the field of view of a localization camera 3 which tracks the marker arrays in real time.

Under certain circumstances, the surgeon may wish to remove a marker array.

In some situations, depending on the position and orientation of the robot, a conflict (mechanical interference) may arise between the tool and a marker array attached to the patient. For example, during knee arthroplasty, in case of a conflict of the tool with the tibial marker array during a femoral cut, the surgeon may remove the tibial marker array to finish the cut, the motion compensation being made using the femoral marker array.

In some situations, a marker array may be dirty due to the projection of blood or other liquids, which may hinder the detection of the markers by the localization camera. The marker array may thus have to be cleaned up, which may be done more easily if the marker array is disconnected from the array fixation.

However, if the marker array to be removed is being tracked by the localization camera to implement a given surgical step, the robot follows the marker array to compensate relative motion. There is thus a risk that, when the marker array is removed from the array fixation, the robot performs a large movement which may hurt the patient or the surgeon.

SUMMARY OF THE DISCLOSURE

It would thus be desirable to determine a method allowing safely disassembling a marker array from an array fixation.

Embodiments relate to a method for disassembling a marker array comprising at least three optical markers arranged according a determined array geometry configured to be tracked by a localization camera from an array fixation to which the marker array is connected, the method comprising, prior to or during disconnecting the marker array from the array fixation, actuating a mechanism configured to selectively modify the array geometry so as to unable tracking of the marker array by the localization camera.

In some embodiments, the mechanism may be configured such that disconnecting the marker array from the array fixation is only possible after the array geometry has been modified.

In some embodiments, the mechanism may be configured to selectively modify the array geometry, and disconnecting the marker array from the array fixation triggers actuation of said mechanism.

In some embodiments, the mechanism is configured to selectively modify the array geometry, and actuation of said mechanism enables disconnecting the marker array from the array fixation.

The marker array may comprise a first part and a second part reproducibly attached to the first part, each of the first and second parts comprising at least one of the optical markers, and the method comprises modifying the geometry of the marker array by separating the second part from the first part.

Alternatively, the marker array may comprise a first part and a second part articulated to the first part, at least one of the first and second parts comprising at least one marker, and the geometry of the marker array is modified by moving the first part relative to the second part between an unfolded position wherein the array geometry is detectable by the camera and a folded position wherein the array geometry is undetectable by the camera as the marker array is disconnected from the array fixation.

Alternatively, the mechanism may comprise a movable member configured to selectively mask at least one marker.

Embodiments relate to a marker array assembly including:

- a marker array comprising at least three optical markers arranged according to a determined array geometry configured to be tracked by a localization camera, and
- an array fixation reversibly connectable to the marker array, wherein at least one of the marker array and the array fixation comprises a mechanism configured to selectively modify the array geometry so as to render the array undetectable by the camera when the marker array is disconnected from the array fixation.

In some embodiments, the mechanism is configured so that disconnection of the marker array from the array fixation triggers actuation of said mechanism.

According to an embodiment, the marker array comprises at least a first part and a second part separable from each other, each of the first and second parts comprising at least one of the optical markers, and the mechanism comprises a reproducible fixation of the second part to the first part.

According to an embodiment, the marker array comprises a first part and a second part, at least one of the first and second parts comprising at least one marker, and the mechanism comprises an articulated shaft connecting the first part and the second part between a folded position wherein the array geometry is not detectable by the camera and an unfolded position wherein the array geometry is detectable by the camera, the array fixation being configured to guide the articulated shaft from the unfolded position to the folded position as the marker array is disconnected from the array fixation.

According to an embodiment, the mechanism comprises a slidable portion comprising a window, said slidable portion being movable between a first position wherein the slidable portion covers a marker and a second position wherein the window uncovers said marker, the slidable portion being urged to the first position by a spring, the mechanism being configured such that when the marker array is connected to the array fixation, the slidable portion is caused by the array fixation to move to the second position and when the marker array is disconnected from the array fixation, the slidable portion moves to the first position.

In some embodiments, the mechanism is configured so that actuation of said mechanism enables disconnecting the marker array from the array fixation.

According to an embodiment, the mechanism comprises a slide movable between an extended position where a cover portion of the slide covers a marker and a retracted position where said marker is uncovered, the slide further comprising a leg portion extending along a translation direction of the slide and a ring portion located between the cover portion and the leg portion, the marker array being connected to the array fixation by a nut, the array fixation comprising a flange, wherein in the retracted position the leg portion engages the flange and the nut is enclosed in the ring portion.

In some embodiments, the mechanism comprises a member movable relative to the marker array to selectively cover at least one marker.

Embodiments relate to a surgical system for treating an anatomical structure, comprising:
- a robot carrying a surgical tool operable to treat the anatomical structure and configured to compensate in real time relative movements of the robot and the anatomical structure,
- at least one marker array assembly as described above, the marker array being configured to be rigidly attached to the anatomical structure, the robot and/or the surgical tool, by the array fixation.

The surgical system may further comprise a localization camera configured to detect the array geometry of each marker array and to track in real time a position and orientation of the anatomical structure and of the robot and/or the surgical tool.

BRIEF DESCRIPTION OF THE FIGURES

Further embodiments and advantages will be described in the following detailed description, with reference to appended drawings wherein.

DETAILED DESCRIPTION OF EMBODIMENTS

Figure 1:
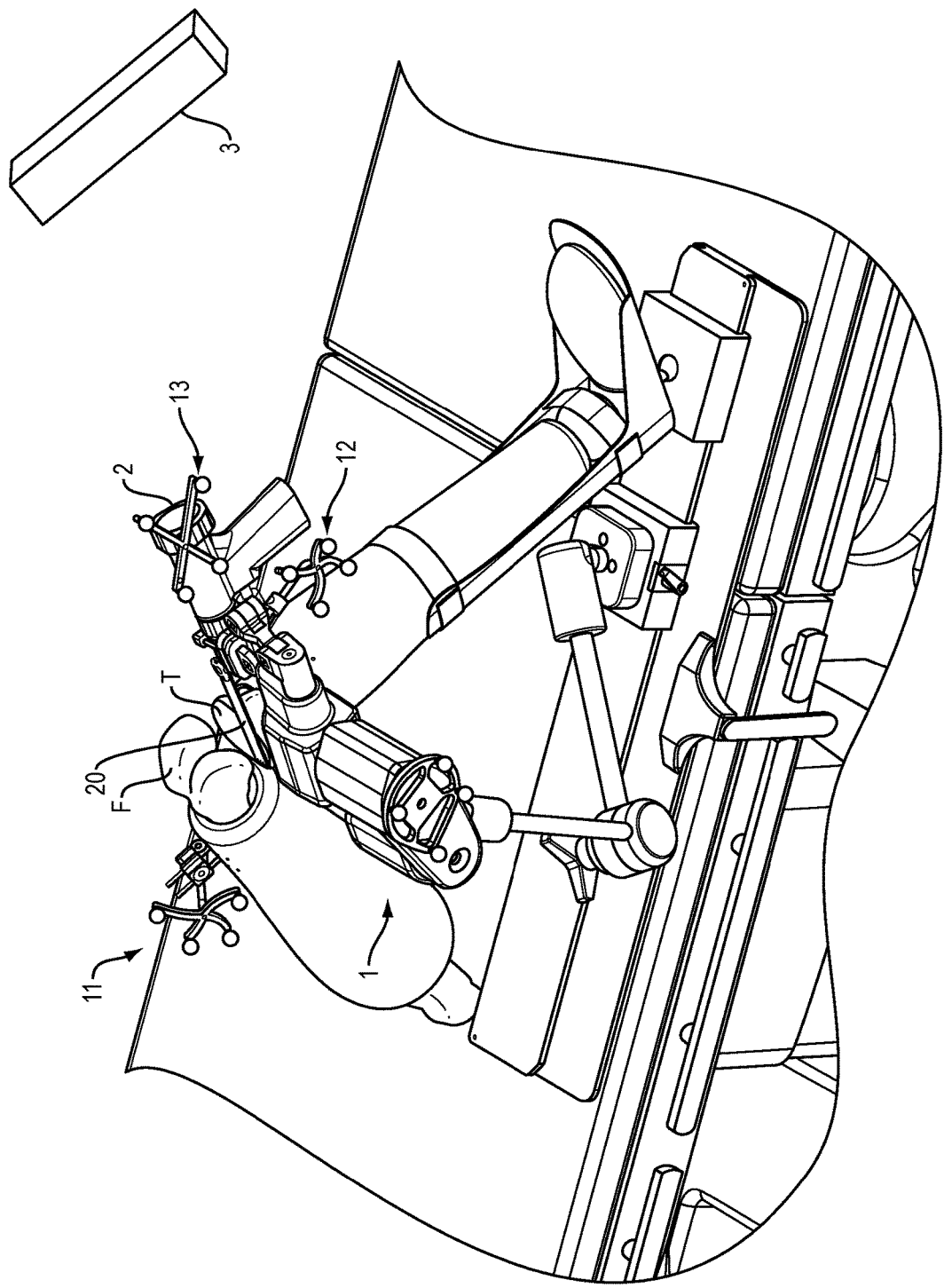
FIG. 1 illustrates a robot providing real time compensation when performing cuts in a knee arthroplasty procedure.

The marker array comprises at least three optical markers.

The markers are preferably passive (e.g. in the form of reflective elements such as spheres) but they may otherwise be active (e.g. LEDs). The marker array may be detected by a camera of a localization system, whose technology depends on the type of markers used in the marker array.

Said three or more markers are arranged according to a determined array geometry which is trackable by the localization camera. Based on said geometry, the localization system is capable of determining the position and orientation of the marker array relative to the camera. However, if some of the markers are completely or partially hidden, such that only one or two markers are visible by the camera, the localization system is not able of detecting the array geometry.

Such a marker array may be used in a surgical system for treating an anatomical structure. Said system may in particular comprise a robot carrying a surgical tool operable to treat the anatomical structure and configured to compensate in real time relative movements of the robot and the anatomical structure.

The marker array may be attached to a patient's bone, a robot and/or a surgical tool by means of an array fixation. The design of the array fixation may depend on the object (bone, tool or robot) to which it has to be attached. For example, the array fixation may include a pin, a clamp . . . . Attaching the array fixation to the object is a preliminary step that does not form part of the present disclosure.

The marker array is connected to the array fixation to form a marker array assembly. Advantageously, the connection between the marker array and the array fixation is reproducible, which means that there exists a unique relative position and orientation of the marker array relative to the array fixation. Said connection may include a magnetic system, a clip system or any other easy to use connection means.

The surgical system comprises a localization camera configured to detect the array geometry of each marker array and to track in real time a position and orientation of the anatomical structure and of the robot and/or the surgical tool.

Prior to or during disconnecting the marker array from the array fixation, an operator has to actuate a mechanism configured to selectively modify the array geometry so as to unable tracking of the marker array by the localization camera.

In some embodiments, disconnection of the marker array from the array fixation is only possible after the array geometry has been modified.

In some embodiments, the marker array may comprise a mechanism configured to selectively modify the array geometry, and disconnection of the marker array from the array fixation triggers actuation of said mechanism.

In other embodiments, the marker array may comprise a mechanism configured to selectively modify the array geometry, and actuation of said mechanism enables disconnection of the marker array from the array fixation.

In some embodiments, the mechanism comprises a movable member configured to selectively mask at least one marker of the marker array.

Several embodiments of the marker array assembly will be described below.

Figure 2:
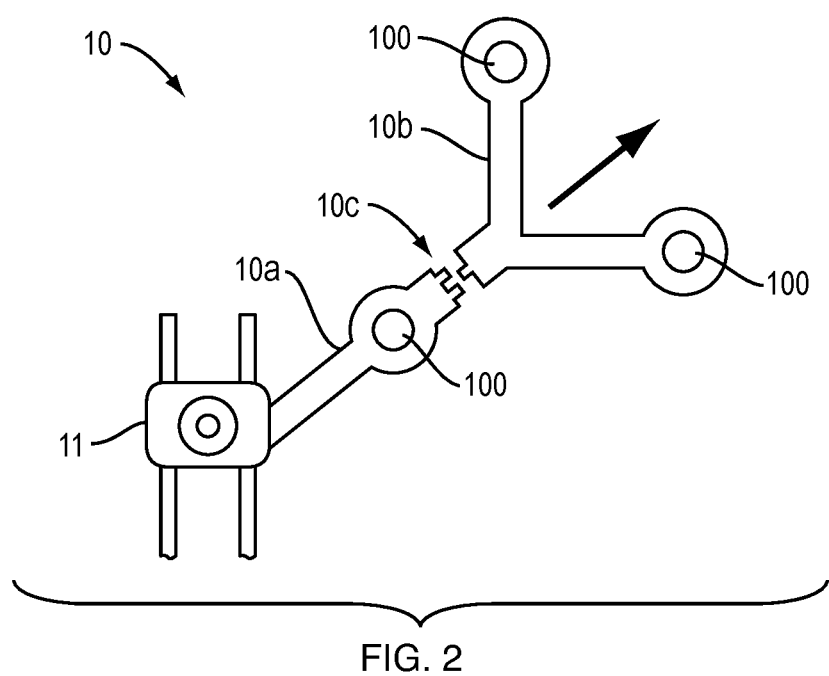
FIG. 2 illustrates a first embodiment of a marker array assembly.

In a first embodiment shown on FIG. 2, the marker array 10 comprises a first part 10a and a second part 10b reproducibly attached to the first part, each of the first and second parts comprising at least one of the optical markers 100. The first part 10a is fixed to an array fixation 11 which is configured to be rigidly attached to an anatomical structure of the patient or to the surgical tool or to the robot.

In this way, when an operator removes the second part from the first part, at least one marker is separated from the other markers, and the geometry of the array is modified. Said modification of the geometry impedes detection of the marker array by the localization system. In such case, the robot and/or the surgical tool may stop automatically for safety reasons.

The reproducible fixation 10c may thus be seen as a mechanism configured to selectively modify the array geometry so as to unable tracking of the marker array by the localization camera. Said reproducible fixation may comprise an indexing feature (not shown) providing a unique orientation of the second part relative to the first part. The reproducible fixation may also be configured so as to allow the second part from being separated from the first part without requiring any tool. For example, the reproducible fixation may include a magnet, clips, etc.

Preferably, the first part 10a, which remains fixed to the array fixation 11, comprises only one marker 100, the other markers being arranged on the second part 10b, which may be more cumbersome than the first part 10b. For example, the first part 10a may be shaped as a short bar to which one marker 100 is attached, whereas the second part 10b may be formed of a plurality of branches each comprising at least one marker 100. In this way, the size of the part which remains attached to the anatomical structure, the robot or the surgical instrument is minimized.

Besides, the fixation of the first part to the array fixation may be stronger or more complex than the fixation of the second part to the first part. In this way, the user will tend to remove the second part from the assembly of the array fixation and marker array, rather than remove the whole marker array from the array fixation.

Figure 3A:
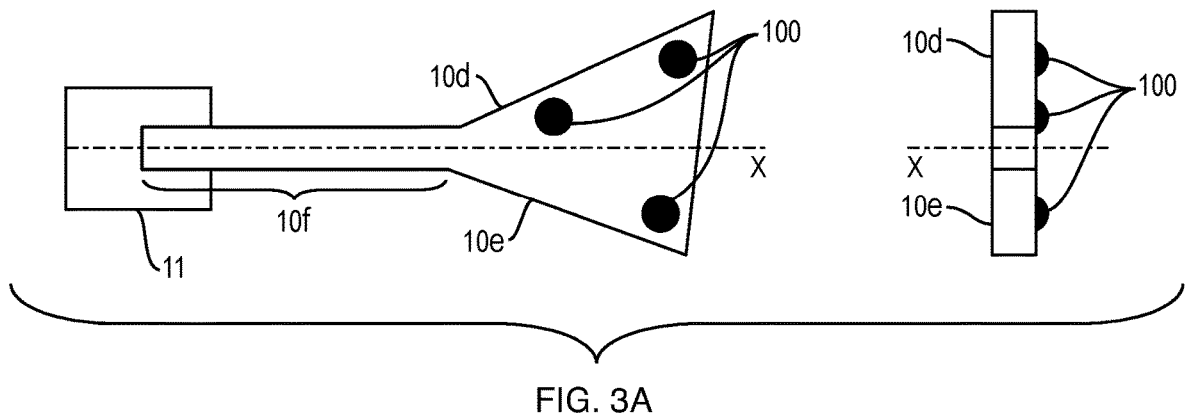
FIGS. 3A-3C illustrate a second embodiment of a marker array assembly, in detectable and undetectable configurations of the array geometry.
Figure 3B:
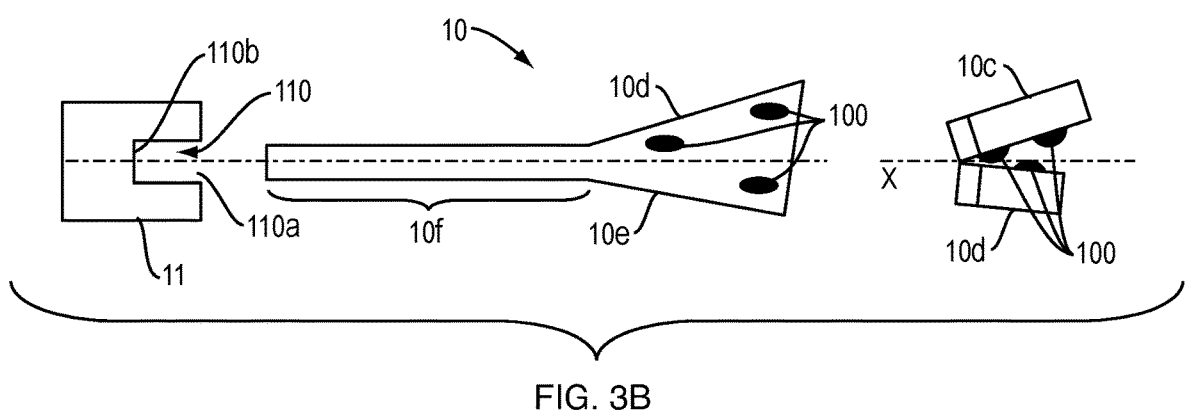
Figure 3C:
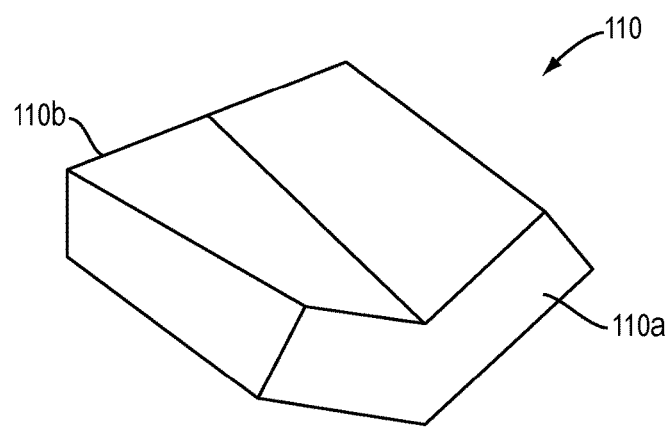

In a second embodiment shown on FIGS. 3A-3C, the marker array comprises a first part 10d and a second part 10e articulated to the first part according to a hinge axis X, at least one of the first and second parts comprising at least one marker 100. The marker array is connected to an array fixation 11, the array fixation comprising a groove 110 extending along the axis X to receive a shaft 10f of the marker array 10.

The geometry of the marker array may be modified by moving the first part 10d relative to the second part 10e between an unfolded position (see FIG. 3A) wherein the array geometry is detectable by the camera and a folded position (see FIG. 3B) wherein the array geometry is undetectable by the camera as the marker array 10 is disconnected from the array fixation 11.

The mechanism causing said movement of the first part relative to the second part is based on a specific shape of the connection between the array fixation and the marker array, said shape being designed so as to bring the marker array into the folded position as the operator removes the marker array from the array fixation. Conversely, the marker array is brought into the unfolded position as the operator engages the marker array with the array fixation.

For example, the shaft 10f of the marker array, which extends from the first and second parts 10d, 10e of the marker array and is thus articulated according to the axis X, and the groove 110 of the array fixation adapted to receive the articulated shaft have complementary shapes that allow said unfolding or folding of the marker array as the marker array is engaged or disengaged from the array fixation. As shown in FIG. 3C, which represents the inner volume of the groove 110, the groove 110 comprises an evolutive shape between a first end 110a through which the shaft 10f is inserted into the groove and a second end opposite to the first end 110b. The articulated shaft 10f, which is guided by the evolutive shape of the groove, is caused to fold or unfold depending on its position relative to the array fixation.

Figure 4A:
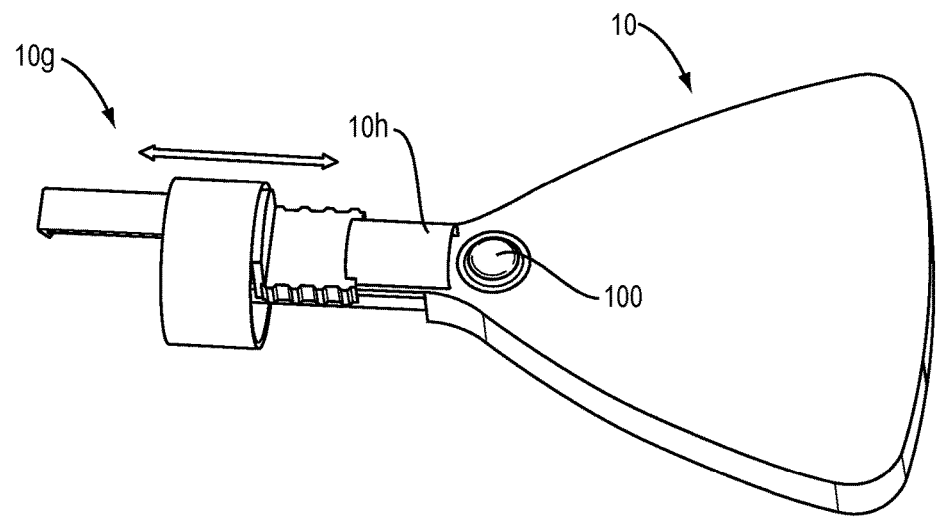
FIGS. 4A-4D illustrate a third embodiment of a marker array assembly.
Figure 4B:
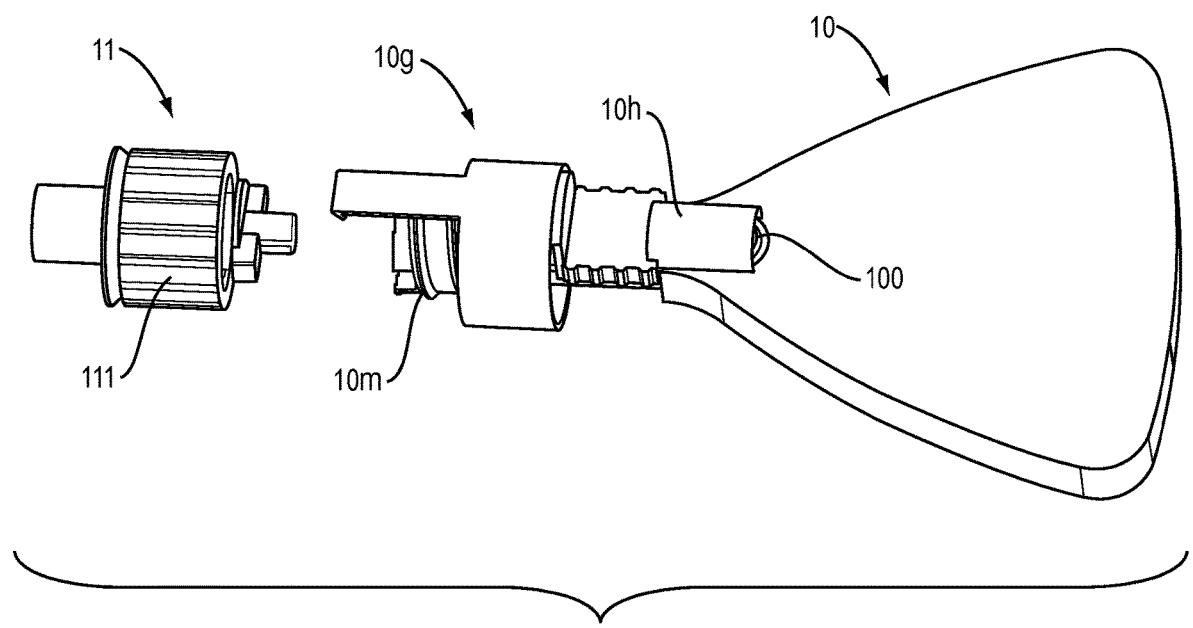

In a third embodiment shown on FIGS. 4A-4D, the marker array 10 comprises a slide 10g which is configured to translate in the direction indicated by the arrow between a retracted position (see FIG. 4A) in which all the markers of the marker array are uncovered and an extended position (see FIG. 4B) where a cover portion 10h of the slide 10g covers a marker 100. Although only said marker 100 is represented in FIGS. 4A-4D, the marker array comprises at least two additional markers forming a known array geometry. The slide 10g is urged by a spring (not shown) so that in the absence of any external load exerted onto the slide, the cover portion 10h covers the marker 100 as shown in FIG. 4B.

The slide 10g further comprises a leg portion 10j extending along the translation direction of the slide and a ring portion 10i located between the cover portion 10h and the leg portion 10j.

Figure 4C:
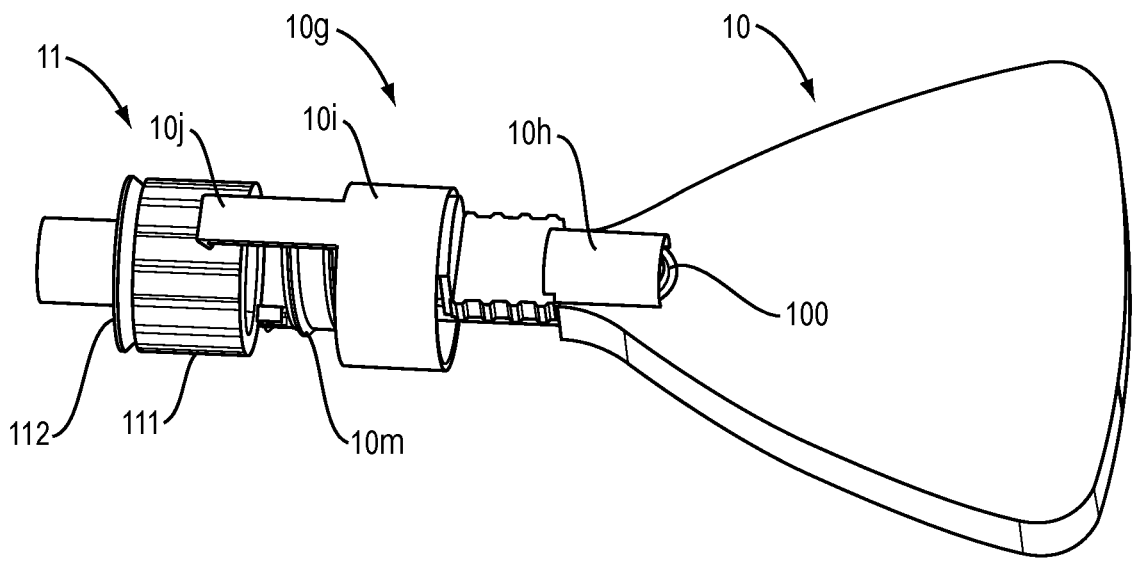

The marker array 10 further comprises a threaded portion 10m configured to be screwed onto the array fixation 11 via a nut 111. Only the part of the array fixation configured for the connection with the marker array is shown in FIGS. 4B-4D.

The array fixation 11 further comprises a flange 112 which extends radially relative to the translation direction of the slide 10g.

As the nut 111 is being screwed onto the threaded portion 10m of the marker array 10 (see FIG. 4C), the nut 111 moves in the direction of the ring portion 10i of the slide until a stop (not shown) indicating that the assembly is completed.

Figure 4D:
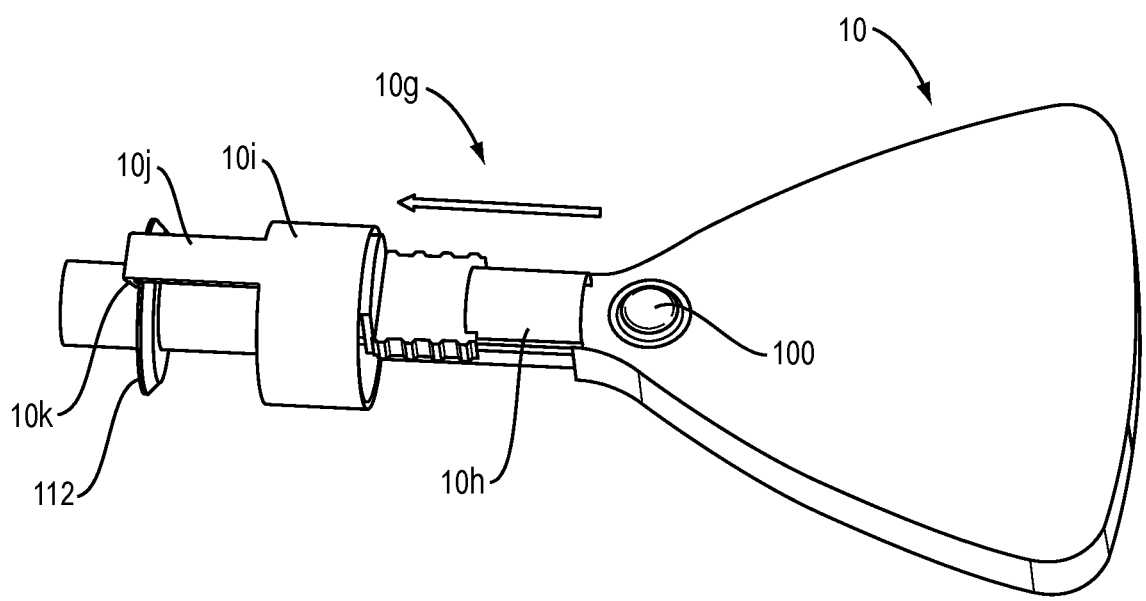

In order to uncover the marker 100 and thereby allowing the array geometry to be detectable by the localization camera, an operator has to translate the slide 10g in the direction of the arrow represented in FIG. 4D so as to snap the leg portion 10j onto the flange 112 thanks to a clip 10k formed in an inner surface of the leg portion 10j. As a result, the slide is retained in the retracted position against the spring force. In this retracted position, the nut 111 is enclosed in the ring portion 10i of the slide.

Thus, in order to access the nut 111 to disconnect the marker array 10 from the array fixation 11, the operator has to unsnap the leg portion 10j from the flange 112. The slide 10g is thus urged to the extended position by the spring, thereby providing access to the nut 111 and at the same time covering the marker 100.

Figure 5A:
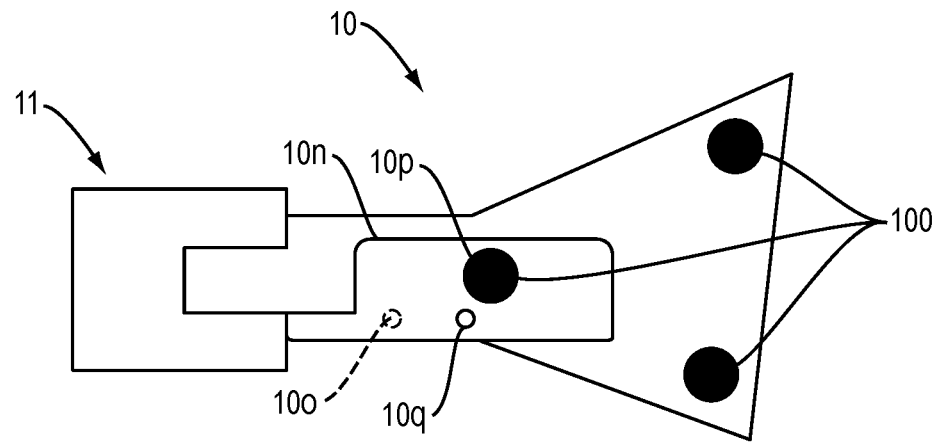
FIGS. 5A-5B illustrate a fourth embodiment of a marker array assembly.
Figure 5B:
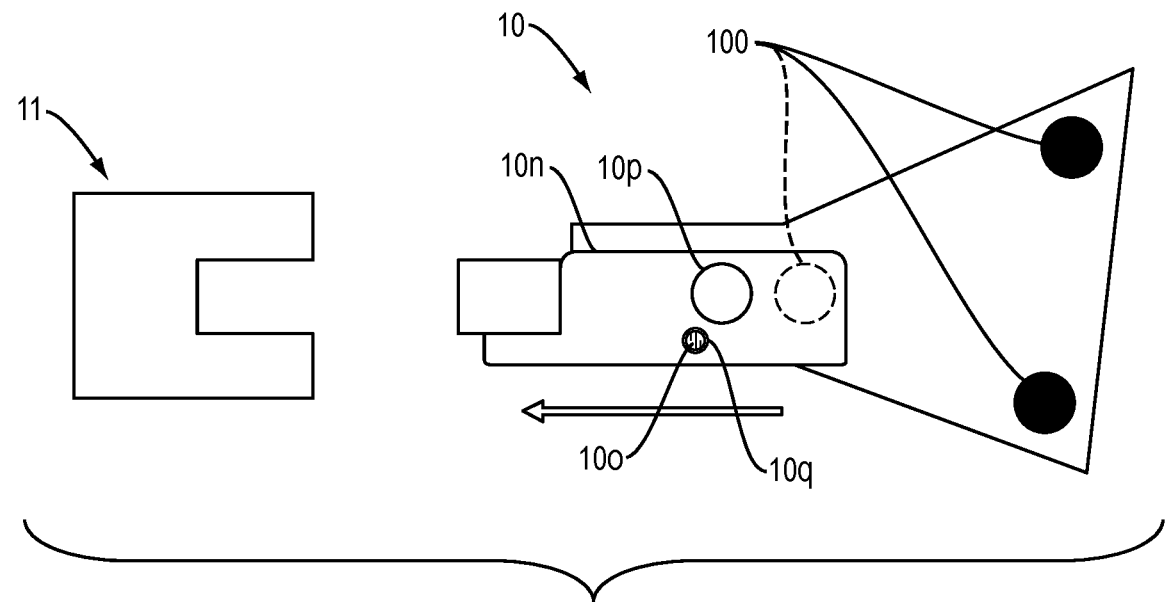

In a fourth embodiment shown on FIGS. 5A and 5B, the marker array 10 comprises a slidable portion 10n comprising a window 10p. Said slidable portion 10n is movable between a first position wherein the slidable portion covers a marker 100 (see FIG. 5B) and a second position wherein the window 10p uncovers said marker (see FIG. 5A), the size of the window being greater than the size of the marker. The slidable portion 10n is urged to the first position by a spring (not shown) according to the direction of the arrow. The slidable portion may be retained in said first position by a ball 10o mounted on a spring (not shown) engaging a housing 10q of the slidable portion.

When the marker array 10 is connected to the array fixation 11 (see FIG. 5A), the slidable portion is caused by the array fixation to move to the second position, thereby placing the window 10p in front of the marker 100 which was initially hidden by the slidable portion. The array geometry may thus be detected by the localization camera.

If the operator disconnects the marker array 10 from the array fixation 11, the slidable portion 10n is moved to the first position by the spring, thereby covering the marker 100.

Figure 6A:
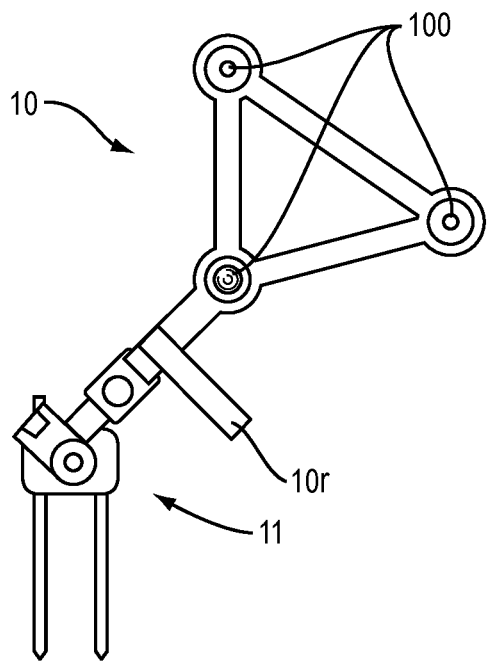
FIGS. 6A-6C illustrate a fifth embodiment of a marker array assembly, respectively in locked, unlocked and disassembled configurations.
Figure 6B:
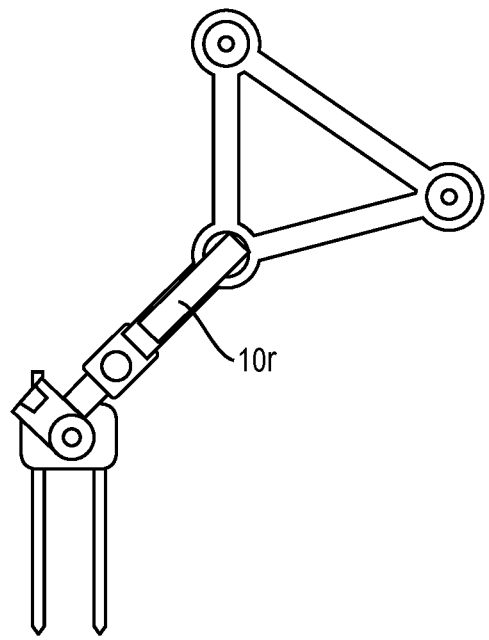
Figure 6C:
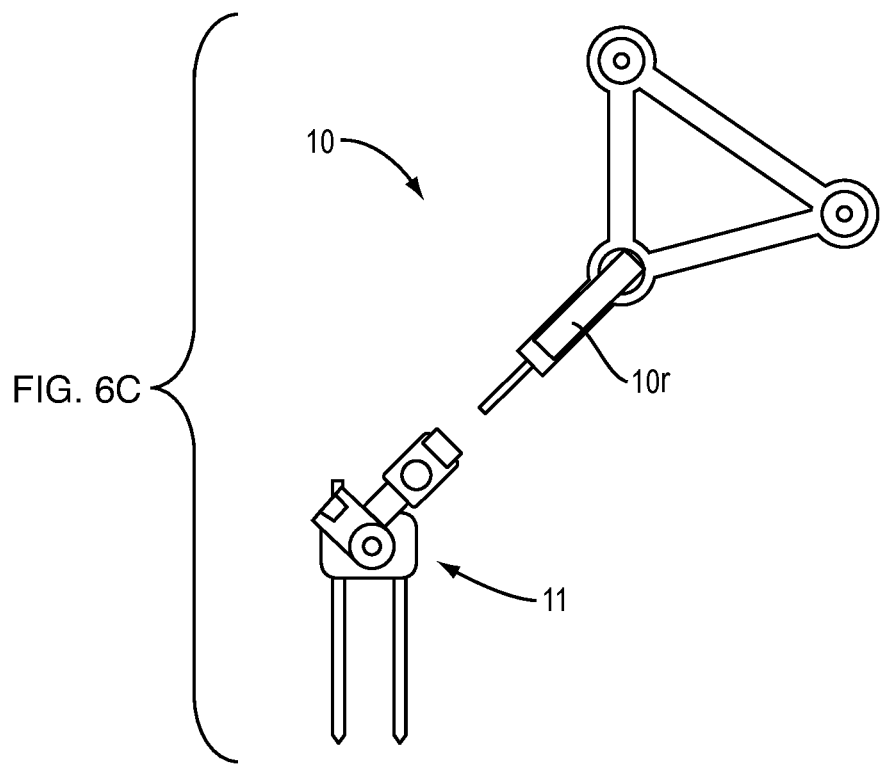

In a fifth embodiment shown of FIGS. 6A-6C, the marker array 10 comprises an arm 10r movable between a first position wherein all the markers are uncovered (see FIG. 6A) and a second position wherein the arm 10r covers at least one marker 100 (see FIG. 6B). In the illustrated embodiment, the arm 10r is pivotable but in other embodiments it may be slidable.

However, this fifth embodiment is less preferred since it does not prevent the operator from removing the marker array without covering the at least one marker. The operator thus has to be specifically trained to move the arm 10r to cover the at least one marker before disconnecting the marker array 10 from the array fixation 11 as shown in FIG. 6C.

Of course, the illustrated embodiments are not intended to be limitative.

REFERENCES

WO 2018/103945

The invention claimed is:

1. A method for disassembling a marker array, the marker array having at least three optical markers arranged according to a determined array geometry configured to be detected by a localization camera, from an array fixation to which the marker array is connected, the method comprising:
providing a robot carrying a surgical tool operable to treat an anatomical structure of a patient, wherein the array fixation is attached to the anatomical structure, the robot, or the surgical tool, and wherein the robot is configured to compensate in real time for relative movement between the robot and the anatomical structure, the movement being detected by the localization camera only when all of the optical markers are visible to the localization camera; and
prior to or during disconnecting the marker array from the array fixation, actuating a mechanism configured to selectively obscure at least one optical marker, thereby modifying the array geometry of the marker array so as to disable detection of the marker array by the localization camera and thus real time compensation for movement.

2. The method of claim 1, wherein the mechanism is configured such that disconnecting the marker array from the array fixation is only possible after the array geometry has been modified.

3. The method of claim 1, wherein the mechanism is configured such that disconnecting the marker array from the array fixation triggers actuation of said mechanism.

4. The method of claim 1, wherein the mechanism is configured such that actuation of said mechanism enables disconnecting the marker array from the array fixation.

5. The method of claim 1, wherein the marker array comprises a first part and a second part articulated to the first part, at least one of the first and second parts comprising at least one marker, and the geometry of the marker array is modified by moving the first part relative to the second part between an unfolded position wherein the array geometry is detectable by the localization camera and a folded position wherein the array geometry is undetectable by the localization camera as the marker array is disconnected from the array fixation.

6. The method of claim 1, wherein the mechanism comprises a hinge disposed between a first part and a second part of the marker array, such that the first part and the second part are folded along the hinge to obscure at least one optical marker.

7. The method of claim 1, wherein the surgical tool is a saw, a burr, or a drill bit.

8. The method of claim 1, wherein the mechanism comprises a movable member configured to selectively obscure the at least one optical marker.

9. The method of claim 8, wherein the movable member is a pivotable cover.

10. The method of claim 8, wherein the movable member is a slidable cover.

11. The method of claim 10, wherein the slidable cover further comprises a window, wherein in a first position, the at least one optical marker is visible to the localization camera through the window, and in a second position, the at least one optical marker is not visible to the localization camera.

12. A surgical system for treating an anatomical structure, comprising:
a marker array having at least three optical markers arranged according to a determined array geometry;
a localization camera for detecting a position and orientation of the marker array;
a robot carrying a surgical tool operable to treat the anatomical structure and configured to compensate in real time for relative movement between the robot and the anatomical structure, the movement being detected only when all of the optical markers are visible to the localization camera; and
an array fixation attached to the anatomical structure, the robot, or the surgical tool, the marker array configured to be removably attached to the array fixation;
wherein the marker array further comprises a cover to engage to selectively obscure at least one optical marker, thereby modifying the array geometry of the marker array so as to disable detection of the marker array by the localization camera and thus real time compensation for movement, and wherein the cover is engaged prior to or during detaching the marker array from the array fixation.

13. The surgical system of claim 12, wherein the cover is moved pivotably to obscure at least one optical marker.

14. The surgical system of claim 12, wherein the cover is folded over the at least one optical marker to obscure at least one optical marker.

15. The surgical system of claim 12, wherein the surgical tool is a saw, a burr, or a drill bit.

16. The surgical system of claim 12, wherein the cover is moved slidably to obscure at least one optical marker.

17. The surgical system of claim 16, wherein the cover further comprises a window, wherein in a first position, the at least one optical marker is visible to the localization camera through the window, and in a second position, the at least one optical marker is not visible to the localization camera.

18. A surgical system for treating an anatomical structure, comprising:
   a marker array having at least three optical markers arranged according to a determined array geometry, the marker array comprising a first part and a second part attached to the first part, each of the first and second parts comprising at least one of the optical markers;
   a localization camera for detecting a position and orientation of the marker array;
   a robot carrying a surgical tool operable to treat the anatomical structure and configured to compensate in real time for relative movement between the robot and the anatomical structure, the movement being detected only when all of the optical markers are visible to the localization camera; and
   an array fixation attached to the anatomical structure, the robot, or the surgical tool, at least a part of the marker array being attached to the array fixation;
   wherein the array geometry of the marker array is modified by separating the second part from the first part, thereby disabling detection of the marker array by the localization camera and thus real time compensation for movement, and wherein the array geometry of the marker array is modified prior to or during detaching the first and second parts of the marker array.

19. The surgical system of claim 18, further comprising an indexing feature for providing an orientation of the second part relative to the first part.

20. The surgical system of claim 18, wherein the surgical tool is a saw, a burr, or a drill bit.

* * * * *